(12) United States Patent
Yufa

(10) Patent No.: US 7,573,573 B1
(45) Date of Patent: Aug. 11, 2009

(54) METHOD AND PARTICLE MEASURING AND COUNTING APPARATUS WITH SELECTABLE CHANNELS OF A SPECIMEN FLOW

(76) Inventor: Aleksandr L. Yufa, 698 Cypress Ave., Colton, CA (US) 92324

( * ) Notice: Subject to any disclaimer, the term of this patent is extended or adjusted under 35 U.S.C. 154(b) by 71 days.

(21) Appl. No.: 11/706,648

(22) Filed: Feb. 13, 2007

Related U.S. Application Data

(62) Division of application No. 11/128,780, filed on May 13, 2005, now Pat. No. 7,439,855.

(51) Int. Cl.
*G01N 15/02* (2006.01)
*G01N 21/00* (2006.01)

(52) U.S. Cl. .................. 356/336; 356/335; 356/337; 356/436; 356/440

(58) Field of Classification Search ............ None
See application file for complete search history.

(56) References Cited

U.S. PATENT DOCUMENTS

| | | | | |
|---|---|---|---|---|
| 3,462,608 A | * | 8/1969 | Gagnon, Jr. et al. | 250/576 |
| 4,473,296 A | * | 9/1984 | Shofner et al. | 356/336 |
| 5,098,657 A | * | 3/1992 | Blackford et al. | 422/73 |
| 5,296,910 A | * | 3/1994 | Cole | 356/28.5 |
| 5,456,102 A | * | 10/1995 | Moorehead | 73/1.24 |
| 5,767,967 A | * | 6/1998 | Yufa | 356/336 |
| 5,946,091 A | * | 8/1999 | Yufa | 356/336 |
| 6,525,807 B1 | * | 2/2003 | Morikawa et al. | 356/72 |
| 6,567,157 B1 | * | 5/2003 | Flagan et al. | 356/37 |
| 2003/0042213 A1 | * | 3/2003 | Hard | 210/807 |

* cited by examiner

*Primary Examiner*—Michael A Lyons
*Assistant Examiner*—Gordon J Stock, Jr.

(57) ABSTRACT

The improved method and particle measuring and counting apparatus with the specimen selectable channels flow provide the analysis of the environmental condition related to contamination and pollution, and particularly provide precise measuring and counting of particles. The improved apparatus includes processor-controller, pump, specimen flowmeter, and the selectable channel specimen flow system comprising the channel valving device, filters, and particle monitor.

7 Claims, 2 Drawing Sheets

METHOD AND PARTICLE MEASURING AND COUNTING APPARATUS WITH SELECTABLE CHANNELS OF A SPECIMEN FLOW

CROSS-REFERENCE TO RELATED APPLICATION

This is a Divisional Application of U.S. patent application Ser. No. 11/128,780, filed May 13, 2005, now the U.S. Pat. No. 7,439,855.

FIELD OF THE INVENTION

This invention relates to the apparatus for analysis of environment such as air, gas and/or liquid/fluid, water and, more particularly, can be related to contamination control apparatus, such as particle quantity counting and particle size measuring.

BACKGROUND OF THE INVENTION

The apparatus for analysis of environment, for instance, such as air (gas) particle quantity counting and particle size measuring, or liquid/fluid (water) particle/contamination size measuring and quantity counting, or airborne (gas) particle and/or liquid/fluid (water) contamination sampling, or airborne (gas) particle and/or liquid/fluid (water) contamination concentration analysis, and the other (hereinafter such apparatus will be mentioned as an environmental analyzer, and the air, gas, liquid/fluid, water, etc. will be mentioned as environment), is known.

Such apparatus for analysis of environment, providing airborne, gas and/or liquid/fluid, water quality analysis (analysis of environment) generally comprises a particle detecting means and a data (signals, information) processing means, and can be of two kinds: portable or remote. Generally, the known apparatus mostly includes a single specimen flow channel, detecting means, processing/controlling means, and portable apparatus may include display, sometimes printer, and front panel with the organs for manual control by operator.

For example, it is well known, that integrated circuits (chips) and semiconductors have been produced in "clean rooms". The air in such "clean rooms" should be very well cleaned. The continuing tendencies of improvement in the circuit integration and degree of microminiaturization require corresponding improvements of the environment in "clean rooms" and efficiency and sensitivity of the contamination measuring devices. The sensitivity of the counting and measuring devices should provide the detection of the particles/contaminations (hereinafter particles/contaminations will be mentioned as particle) at least as small as 0.085 μm (micron) or smaller. Such rate requires minimum distortions of the signals. Also, the measurements should be done in the different places of the semiconductor production areas and sometimes in the areas with the difficult access and approach. The same is, for instance, regarding the pharmaceutical, biological industries, etc. where the high environmental condition is required too.

The most common problem inherent in the most environmental analyzers is a non-precise selection of the flow system for the assayed specimen flowing through the detecting system. The most of the known environmental analyzers for airborne (gas) particle and/or liquid (water) contamination control use only one (single) channel for flow of the particles of all sizes.

The bigger particles of the assayed specimen flowing through the single channel may shadow the smaller particles during particles monitoring (detecting) creating a non-precise particle counting.

This deficiency is eliminated by the method and device providing precise particle flow system described in U.S. Pat. No. 5,946,091. The device generally includes an entrance particle flow tubular means connected by an extended entrance particle flow tubular means through a blowing means and flow measuring means to an inlet valved means of the linear-style valving means. The inlet valving means by at least one of a plurality of extended inlet particle flow tubular means is connected through appropriate at least one of a plurality of filters of the inlet filtrating means to the appropriate at least one of a plurality of capillary inlet particle flow means. The detecting system comprises a source of a light beam (laser) and light detection means, etc. Hereinafter the meaning of "light beam" should include without limitations the meanings of "laser" and/or "laser beam", any suitable and adequate visible and/or invisible rays, etc. The at least one of a plurality of capillary outlet particle flow means are connected by an appropriate at least one of a plurality of extended outlet particle flow tubular means to an outlet valving means of valving means, which by an extended exit particle flow tubular means is connected to a purging means. The purging means through outlet filtration means and exit particle flow tubular means is connected to the outside environment. Also, a blowing/pumping means, a flow measuring means, an inlet valving means of the valving means, a detecting system, an outlet valving means of the valving means and a purging means are connected to a control system.

The deficiency of this precise device is a possible high cost of the required plurality of the capillary inlet and outlet particle flow means.

Thus, there is a great need in the art for the improved method and efficient, not expansive environment analyzing apparatus able to provide the precise assayed specimen flow system for the precise particle measuring and counting.

OBJECT AND ADVANTAGES OF THE INVENTION

Accordingly, several objects and advantages of the present invention are to provide the improved method and apparatus for industries needed to provide contamination control in the appropriate areas, etc.

It is the object of the invention to increase efficiency of the environmental analyzers.

It is another object of the invention to increase the precision of the assayed specimen flow system, thereby, increasing the precision of the particle measuring and counting apparatus.

It is further object of the invention to eliminate the shadowing of the smaller particle by the bigger particles at the time of particle monitoring.

Still, further objects and advantages will become apparent from a consideration of the ensuing description accompanying drawings.

SUMMARY OF THE INVENTION

The invention provides a method and particle measuring and counting apparatus with the specimen selectable channels flow.

The improved apparatus provides the airborne, gas and/or liquid/fluid, water quality analysis and generally comprises an environment monitoring (sensing, detecting) system, specimen selectable channel flow (selectable channels) system, and a processing system.

The outside of the environmental analyzer (e.g. particle measuring and counting device) environment, assayed by the pumping means via the entrance flow tubular means, for instance, through the flow measuring means by an extended entrance particle flow tubular means, flows to the inlet portion of the valving means. The control of the pumping means and/or flow measuring means are provided by the processing and control system.

The controllable valving means distributes the air flow (particle flow) from its outlet portion to one of the particle flow channel, depending on the particle size, which is intended for the counting and measuring. Each channel intended for the passage of the particles not exceeding the determine particle size. Further the particles flow by the selected extended inlet particle flow tubular means through the selected particle flow inlet filter of an inlet filtrating means, and through the channel connector, channel connector outlet tubular means, and capillary inlet flow means into monitoring means including the particle detection means (not shown), providing an appropriate output signal, adequate for each particle, following to the processing system for processing. The processing system processes each signal forming the information about particle size and quantity. The analyzed specimen after appropriate filtration is exhausted from the apparatus.

DESCRIPTION OF THE PREFERRED EMBODIMENTS

Here the description of an improved apparatus will be done in statics (as if the components of the improved apparatus are suspended in the space) with description of their relative locations and connections to each other. The description of the improved methods and functional operations of an improved apparatus will be done hereinafter.

Figure 1:
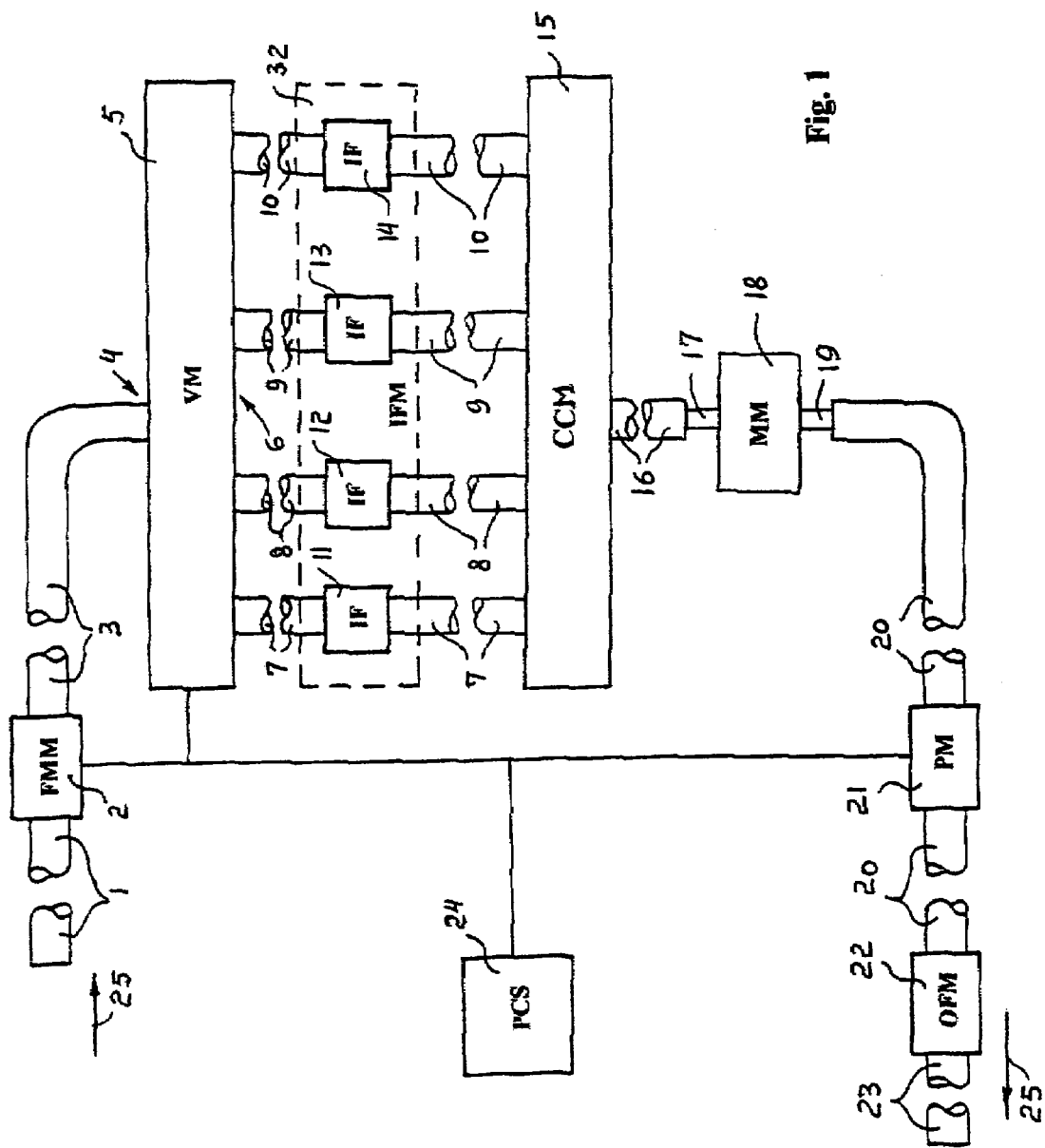
FIG. 1 is a simplified block diagram of the improved apparatus with the specimen selectable channels flow.

FIG. 1 is a simplified block diagram of the improved apparatus with the specimen selectable channels flow. Referring to FIG. 1, the improved apparatus comprises the entrance flow tubular means 1 coupled with the flow measuring means (FMM) 2 which are via the extended entrance particle flow tubular means 3 coupled with the inlet portion 4 of the valving means (VM) 5. The outlet portion 6 (also shown in FIG. 2) by the extended inlet particle flow tubular means 7, 8, 9, 10 (FIG. 1) via the appropriate particle flow inlet filter (IF) 11-14 of the inlet filtrating means (IFM) 32 is coupled with the channel connecting means (CCM) 15, which is via the channel connector outlet tubular means 16 coupled with the capillary inlet flow means 17. The capillary inlet flow means 17 is coupled with monitoring means (MM) 18 including the capillary outlet particle flow means 19. The capillary outlet particle flow means 19 by the extended outlet particle flow tubular means 20 via the pumping means (PM) 21 and outlet filtrating means (OFM) 22 is coupled with the exhaust particle flow tubular means 23. The channel connecting means 15 provides the joining of the particle flow channels (the extended inlet particle flow tubular means, e.g. 7, 8, 9, 10 [FIG. 1] or 7, 8, 9 [FIG. 2]) after filtration into one single flow channel (the inlet flow means 17 in FIGS. 1, 2).

The improved apparatus also includes the processing and control system (PCS) 24 electrically connected to the flow measuring means 2, to the valving means 5 (if control of the valving means is provided automatically/not manually/), to the monitoring means 18, and to the pumping means 21 (the pumping/suction means can be for example presented by blowing means [not shown], suction means [not shown], and/or any other suitable means).

The improved apparatus operates as follows. Referring to FIG. 1, the outside of the improved apparatus environment (for example, an air for particle counting and measuring, but it could be gas, liquid/water, etc.), assayed by the pumping means 21 via the entrance flow tubular means 1 through the flow measuring means 2 and the extended entrance, particle flow tubular means 3, flows in direction 25 to the inlet portion 4 of the valving means 5. The valving means 5 can be of any reasonable design (for instance, non-controllable or controllable/e.g. manually or automatically, etc./), form, configuration, size and color, etc., for example, the valving means 5 can be of in-line (linear/plane-style) channel design (not shown) or more compact rotary design, as show in FIG. 2. The pumping means 21 can be presented by any reasonable means providing the assayed specimen flow through the monitoring means 18 of the detecting means (not shown). For instance, the pump(s), centrifugal blower(s) and/or any purging means, etc. can be used for specimen assaying. The operation of the pumping means 21 and flow measuring means 2 can be controllable, as it is shown in FIG. 1, or non-controllable (not shown). The control of the pumping means 21 and/or flow measuring means 2 can be provided by the processing and control system 24 (see FIG. 1).

The controllable valving means 5 distributes from its outlet portion 6 the air flow (particle flow) to one of M=1, 2, . . . , j, . . . , m particle flow channels, depending on the particle size, which is intended for the counting and measuring. The controllable valving means 5 is presented in FIG. 2 by a rotary-style valving means changing the channels by rotation of the inlet portion 4 in the direction 26 to the appropriate position with the movement down (in direction 25) to provide the air non-leaking connection of the appropriate channel tubular means with the extended entrance particle flow tubular means 3. It should be understood that the valving means are not limited to the described herein and any suitable construction of the valving means can be used.

For example, assume that the selected channel will be the j-th channel (in FIG. 1 conditionally shown four flow channel: the first channel is provided by an extended inlet particle flow tubular means 7, second channel is provided by an extended inlet particle flow tubular means 8, j-th channel is provided by an extended inlet particle flow tubular means 9 and m-th cannel is provided by an extended inlet particle flow tubular means 10). The particles flow by the appropriate extended inlet particle flow tubular means 9 through an j-th particle flow inlet filter 13 of an inlet filtrating means 32, and through a channel connecting means 15, and via the channel connector outlet tubular means 16 and capillary inlet flow means 17 into monitoring means 18.

Figure 2:
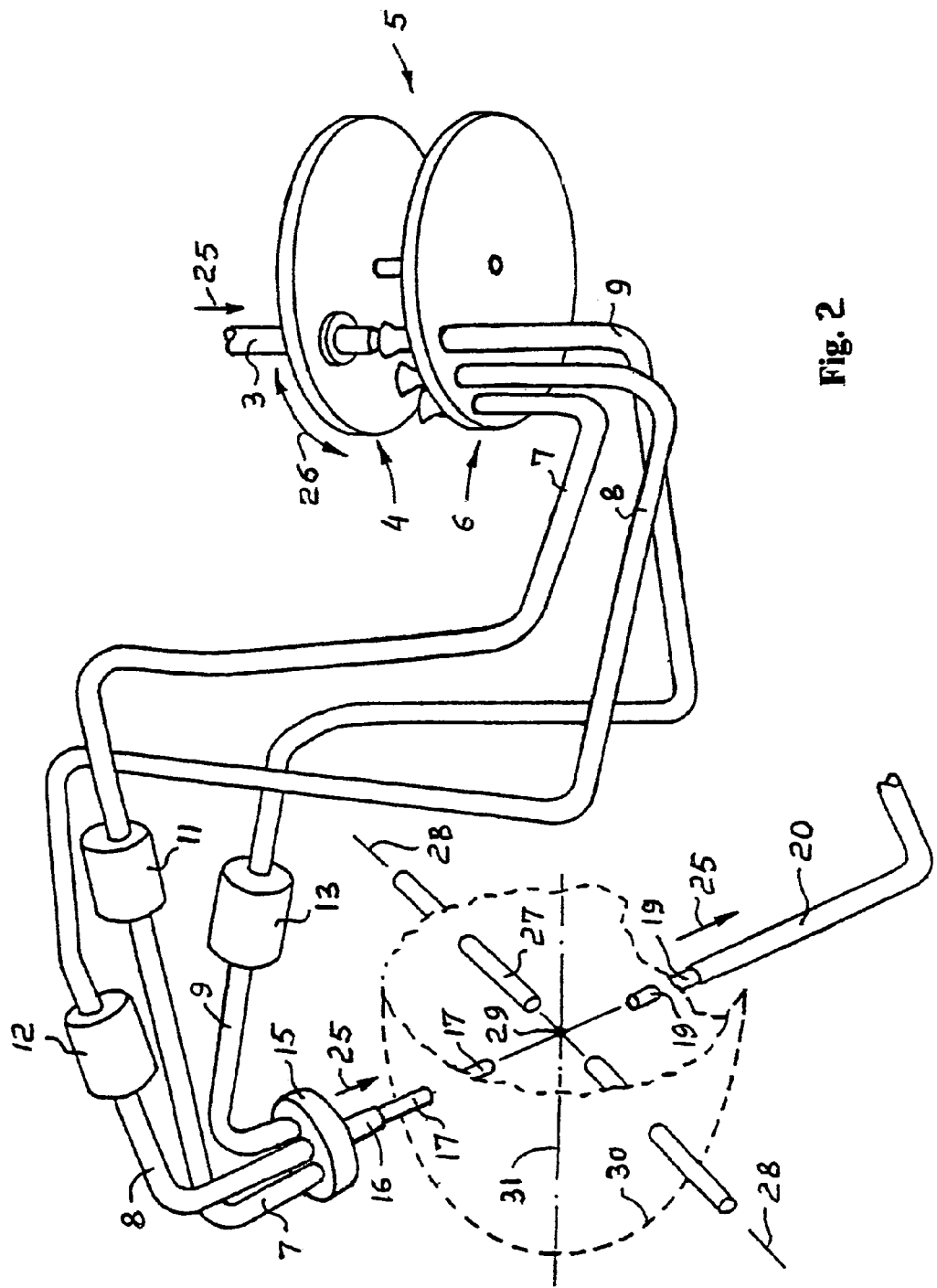
FIG. 2 is a simplified kinematic diagram of the improved specimen flow channels.
Figure 1:
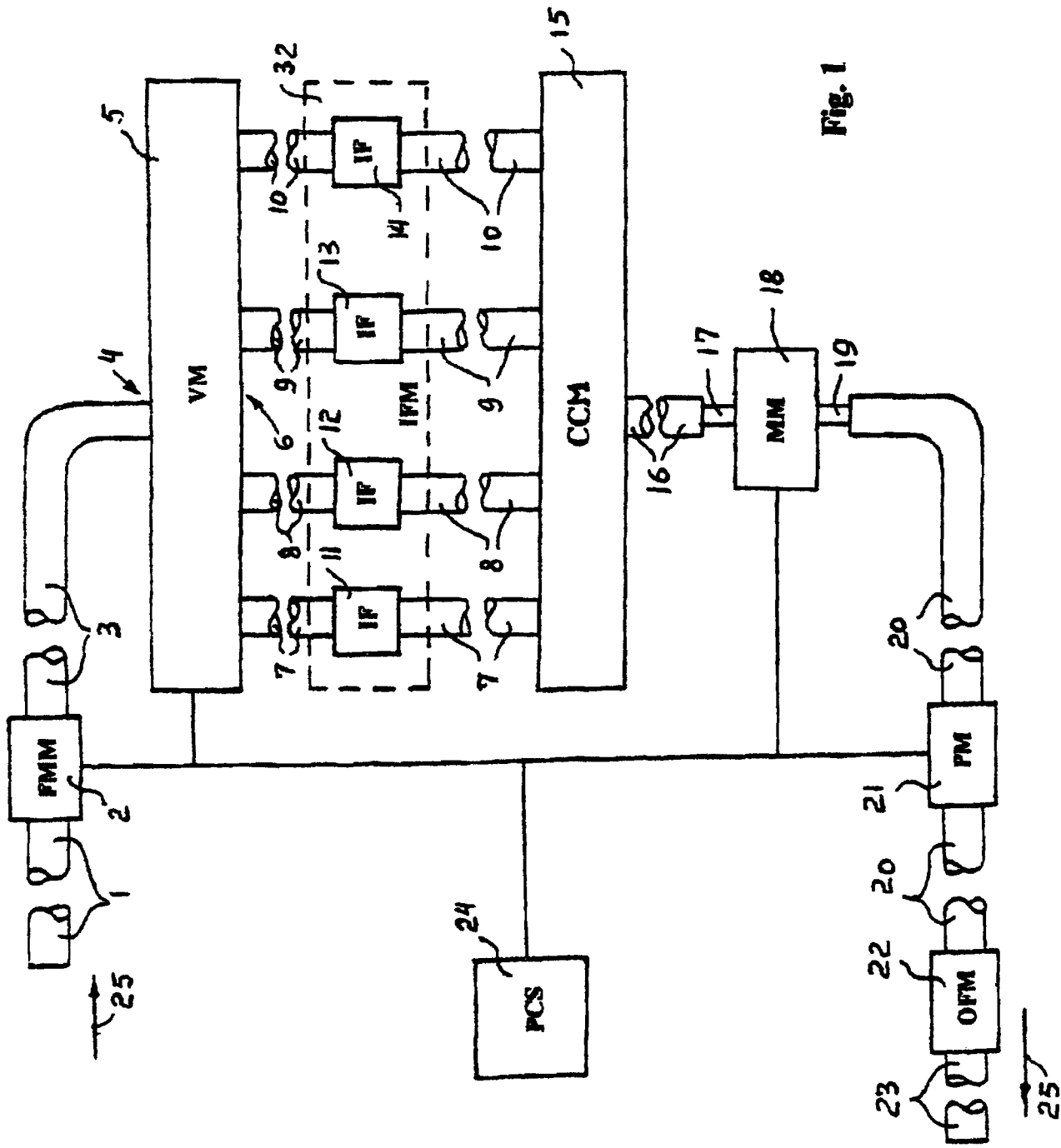

Each particle flow inlet filter 11-14 of the inlet filtrating means 32 is intended for the determined size particles only. It means, for example, if j-th channel is intended for counting and measuring 0.5 μm particles, the particle flow inlet filter 13 filtrates everything (any and all particles) over 0.5 μm, providing a particle sorting for the further passage of already predetermined size particles through the capillary inlet flow means 17. The monitoring means 18 of the contamination detecting system (not shown and further, for instance, the particle detecting system, if the monitored characteristic is the contamination/particle size, etc.) monitors the particles presented in the assayed specimen flow (in the assayed/pumped in/environment) by, for example, a light (laser) beam 27 (e.g. from the power light source or laser, laserdiode, etc.) along axis 28 intersecting the particle flow at the focal point 29. In FIG. 2, the portion of the of the particle monitoring system is conditionally presented by portion of the ellipsoidal mirror 30 with the main axis 31 on which is located focal point (focus) 29. The light scattered from the particle flowing through the focus 29 is detected by the light detecting means (not shown), for instance such as photodetector, photodiode, etc. The light detecting means (not shown) produces an output(s) (e.g. initial signal/s/) effectively indicative of the particle characteristic (e.g. particle size), which flows to the processing and control system 24 for processing (e.g. processing of the initial signals, based on the signals measuring and counting them forming the information about particle size and quantity, displaying the appropriate information, etc.). In FIG. 2 the particle detecting (monitoring) system is presented by a portion of an ellipsoidal mirror, but it could be without limitations any optical systems, e.g. such as paraboloidal and/or spherical mirrors, etc., lens(es) and/or combination of the lenses, or non optical systems e.g. such as the direct detection system and means, etc. Also, in FIG. 2 the particle detecting (monitoring) principle is presented by the scattered light collection, but the direct detection principle, and/or the any other applicable principles of environment analyzing (detection) can be used. It should be understandable, that the use of the light/laser beam (as an example) is not limited to the light only, i.e. any suitable and/or applicable visible and/or invisible rays, and/or a magnetic field and/or an electromagnetic field and/or an electrical field and/or an electrostatic field and/or a radioactivity, etc. could be used. The capillary inlet and outlet particle flow means (e.g. such as 17 and 19) may be presented by the suitable material capillary and/or tubular means.

The improved method provides the steps as it has been described of the above and as follows below. The axis (not shown) of the capillary inlet particle flow means 17 is coincident with the axis (not shown) of the capillary outlet particle flow means 19. The particle, flowing along the capillary particle flow means, as it has been mentioned above intersects a light beam axis 28 on the device axis (optical system axis) 31 at the optic focal point 29, as it is shown in FIG. 2. It is conditionally, as example, shown the three channels (e.g. first 7, second 8, and j-th 9 channels).

By the improved method, the particles of the particle flow pass through the focal point (focus) 29. The initial signals, adequate to the particles, from the light detecting means (e.g. photodetector, photodiode, photomultiplier tubes, etc.—not shown) of the monitoring means 18 follow to the processing and control system 24 for processing, forming data containing information about particle characteristic(s) (e.g. particle size and quantity). The monitored particles flow through capillary outlet particle flow means 19, extended outlet particle flow tubular means 20, pumping means 21 to outlet filtrating means 22. After filtration by the outlet filtrating means 22, the appropriately cleaned specimen is exhausted through the exhaust particle flow tubular means 23 to the outside environment. The air flow is measured by controllable flow measuring means 2, which is also controlled by the processing and control system 24, and information (e.g. processed by the processing and control system 24) about air flow characteristics can be indicated by the terminal means (e.g. displaying means, printing means, etc.) to the operator of the improved apparatus and/or may be recorded (e.g. by the floppy means, click means, E-PROM, etc.—not shown). The displaying, printed and/or recorded data about environment condition may include the information from temperature sensor (not shown) and/or other sensors (e.g. humidity, etc.—not shown). The mentioned sensors may be controllable by processing and control system 24 or non-controllable.

For monitoring of the liquids (drinking water, for example), an improved apparatus can comprise an entire undivided capillary particle flow means (not shown) instead of the capillary inlet 17 and outlet 19 flow means. All capillary flow means including mentioned solid (undivided) capillary flow means can be of any reasonable form and configuration, for example, the square or circular geometric inside/outside form with inside dimensions preferably correlated to the largest predetermined size particle. The capillary particle flow system, as a module of the detecting system of the improved apparatus, can be interchangeable to provide the other needed environmental analysis. The pumping means (specimen suction means) 21, flow measuring means 2 and other sensors (not shown) may operate in the predetermined mode (without control) and/or in controllable (automatic [by processing and control means 24] or manual [by operator]) modes, etc. It is understandable, that, for instance, the flow measuring means 2 can be placed after monitoring means 19 or after pumping means 21, etc.

It should be understood that numerous modifications and variations of the present invention are possible in light of the above teaching and it is also understood, that the above description discloses specific embodiments of the present invention and are for purposes of illustration only without any limitations. There may be other modifications and changes obvious to those of ordinary skill in the art which fall within the scope of the present invention and within scope of the appended claims, the invention may be practiced otherwise than as specifically described herein.

CONCLUSION, RAMIFICATION AND SCOPE

Accordingly the reader will see that, according to the invention, I have provided the effective methods and precise and non-complex apparatus for monitoring of environment, for example, such as the air and/or gas, liquid/fluid and/or water or any other environmental substance(s) and/or object(s), e.g. such as the dust on the surface, etc.

The improved methods and apparatus can provide particle (contamination) precise counting and measuring in the assayed environment eliminating the shadowing the smaller particles by the bigger particles at the time of monitoring.

The improved methods and apparatus provide the variety of the control including, but not limited to manual and automatic. This factor may be very convenient for the improved portable particle measuring and counting apparatus operated by the operator and for remote particle measuring and counting apparatus operated automatically from the distance. The improved specimen (particle) flow provide precise, less complex, and less expensive particle flow system.

While the above description contains many specificities, these should not construed as limitations on the scope of the invention, but as exemplification of the presently-preferred embodiments thereof. Many other ramifications are possible within the teaching of the invention.

For example, the improved methods and apparatus can be successfully used for air/gas and for liquid substances, may be used for the portable and remote environment analyzing apparatus, etc. Also, the improved method can be successfully applied to the apparatus using magnetic, electromagnetic, electrostatic fields and/or other types of the fields, or radioactivity instead of the ray(s) and/or light (laser) beam(s).

Thus, the scope of the invention should be determined by the appended claims and their legal equivalents, and not by examples given.

What is claimed is:

1. A method for measuring and counting of particles illuminated by a light beam or a ray, said method comprising the steps of:

assaying of an environment providing a particle flow;

forming from said particle flow in a valving means a plurality of particle flow channels, each of which is intended for a flow of particles of an appropriate predetermined size;

providing each of said plurality of said particle flow channels with an appropriate filtrating means which provides a filtration of particles which are larger than said particles of said appropriate predetermined size forming a flow channel of said particles of said appropriate predetermined size;

joining flow channels by a channel connecting means forming in said channel connecting means a single flow channel of particles of a predetermined size;

selecting by said valving means from said plurality of said particle flow channels the particle flow channel intended for said flow of said particles of said appropriate predetermined size for said filtration;

providing said flow of said particles of said appropriate predetermined size via the selected particle flow channel through said appropriate filtrating means;

providing a flow of said particles of said appropriate predetermined size from said appropriate filtrating means into said channel connecting means;

providing said flow of said particles of said predetermined size from said channel connecting means along said single flow channel, and wherein said single flow channel provides said flow of said particles of said predetermined size from said channel connecting means through a point within a particle monitoring region of a particle monitoring means for said measuring and counting;

providing a particle monitoring by said particle monitoring means comprising said particle monitoring region through which said flow of said particles of said predetermined size is directed;

directing said light beam or said ray toward said particle monitoring region so that said particles of said predetermined size are monitored in said particle monitoring means by intersecting said particles of said predetermined size by said light beam or said ray at said point within said particle monitoring region;

sensing a light or a pattern created by the flowing particles under influence of said light beam or said ray at said point, and providing an output which is effectively indicative of the size of the monitored particles;

processing said output forming an information about size and quantity of the measured and counted particles.

2. The method of claim 1, wherein said particles of said predetermined size are further monitored by a magnetic field and/or an electromagnetic field and/or an electrical field and/or an electrostatic field and/or a radioactivity, and wherein said monitoring means further provides said sensing of said pattern created under said influence of said magnetic field and/or said electromagnetic field and/or said electrical field and/or said electrostatic field and/or said radioactivity instead of said light beam or said ray.

3. A particle measuring and counting apparatus with selectable channels of a specimen flow includes an entrance flow tubular means coupled with a flow measuring means;

an extended entrance particle flow tubular means coupled with an inlet portion of a valving means and with said flow measuring means;

an outlet portion of said valving means appropriately coupled with a plurality of extended inlet particle flow tubular means, each of which is coupled with an appropriate inlet filter of an inlet filtrating means;

a channel connecting means coupled with the inlet filters of said inlet filtrating means and through an outlet tubular means coupled with a single capillary inlet particle flow means;

a particle monitoring means coupled with said single capillary inlet particle flow means and including a single capillary outlet particle flow means which by an extended outlet particle flow tubular means is coupled with a pumping means, wherein said single capillary inlet particle flows means and said single capillary outlet particle flows means form a flow channel of particles of a predetermined size, and wherein said flow channel of said particles of said predetermined size provides a flow of said particles of said predetermined size, selected by said valving means, from said channel connecting means through said single capillary inlet flow means, a point within a particle monitoring region of said particle monitoring means, and said single capillary outlet particle flow means;

an outlet filtrating means coupled with said pumping means and with an exhaust particle flow tubular means;

a processing and control system electrically connected to said flow measuring means and to said pumping means.

4. The apparatus of claim 3, wherein said valving means is a rotary valving means and is controlled manually, wherein said valving means includes an inlet portion and an outlet portion, and wherein said valving means provides a change of channels by a rotation of said inlet portion of said valving means.

5. The apparatus of claim 4, wherein said valving means, comprising said inlet portion and said outlet portion, further are electrically connected to a processing and control means, and wherein said valving means are further controlled by said processing and control means.

6. The apparatus of claim 3, wherein said flow measuring means is further located between said single capillary outlet particle flow means and said pumping means, and coupled by said extended outlet particle flow tubular means with said pumping means and said single capillary outlet particle flow means which is coupled with said particle monitoring means coupled with said single capillary inlet particle flow means which is coupled with said channel connecting means.

7. The apparatus of claim 3, wherein said flow measuring means is further located between said pumping means and said outlet filtrating means, and coupled with said pumping means and said outlet filtrating means by said extended outlet particle flow tubular means which is coupled with said single capillary outlet particle flow means which is coupled with said particle monitoring means coupled with said single capillary inlet particle flow means.

* * * * *

UNITED STATES PATENT AND TRADEMARK OFFICE
CERTIFICATE OF CORRECTION

| | |
|---|---|
| PATENT NO. | : 7,573,573 B1 |
| APPLICATION NO. | : 11/706648 |
| DATED | : August 11, 2009 |
| INVENTOR(S) | : Aleksandr L. Yufa |

It is certified that error appears in the above-identified patent and that said Letters Patent is hereby corrected as shown below:

In the Drawings

The drawing sheet 1 of 2 consisting of Fig(s) 1 should be deleted and substitute therefore the attached drawing sheet 1 of 2 consisting of Fig(s) 1.

Signed and Sealed this
Fourth Day of September, 2012

David J. Kappos
*Director of the United States Patent and Trademark Office*